(12) United States Patent
Balakin

(10) Patent No.: US 8,045,679 B2
(45) Date of Patent: *Oct. 25, 2011

(54) CHARGED PARTICLE CANCER THERAPY X-RAY METHOD AND APPARATUS

(76) Inventor: Vladimir Balakin, Protvino (RU)

( * ) Notice: Subject to any disclaimer, the term of this patent is extended or adjusted under 35 U.S.C. 154(b) by 114 days.
This patent is subject to a terminal disclaimer.

(21) Appl. No.: 12/492,216

(22) Filed: Jun. 26, 2009

(65) Prior Publication Data

US 2010/0008468 A1  Jan. 14, 2010

Related U.S. Application Data

(60) Provisional application No. 61/137,574, filed on Aug. 1, 2008, provisional application No. 61/192,245, filed on Sep. 17, 2008, provisional application No. 61/203,308, filed on Dec. 22, 2008, provisional application No. 61/188,407, filed on Aug. 11, 2008, provisional application No. 61/209,529, filed on Mar. 9, 2009, provisional application No. 61/188,406, filed on Aug. 11, 2008, provisional application No. 61/189,815, filed on Aug. 25, 2008, provisional application No. 61/208,182, filed on Feb. 23, 2009, provisional application No. 61/201,731, filed on Dec. 15, 2008, provisional application No. 61/208,971, filed on Mar. 3, 2009, provisional application No. 61/205,362, filed on Jan. 21, 2009, provisional application No. 61/134,717, filed on Jul. 14, 2008, provisional application No. 61/134,707, filed on Jul. 14, 2008, provisional application No. 61/201,732, filed on Dec. 15, 2008, provisional application No. 61/198,509, filed on Nov. 7, 2008, provisional application No. 61/134,718, filed on Jul. 14, 2008, provisional application No. 61/190,613, filed on Sep. 2, 2008, provisional application No. 61/191,043, filed on Sep. 8, 2008, provisional application No. 61/192,237, filed on Sep. 17, 2008, provisional application No. 61/201,728, filed on Dec. 15, 2008, provisional application No. 61/190,546, filed on Sep. 2, 2008, provisional application No. 61/189,017, filed on Aug. 15, 2008, provisional application No. 61/198,248, filed on Nov. 5, 2008, provisional application No. 61/198,508, filed on Nov. 7, 2008, provisional application No. 61/197,971, filed on Nov. 3, 2008, provisional application No. 61/199,405, filed on Nov. 17, 2008, provisional application No. 61/199,403, filed on Nov. 17, 2008, provisional application No. 61/199,404, filed on Nov. 17, 2008, provisional application No. 61/055,395, filed on May 22, 2008, provisional application No. 61/055,409, filed on May 22, 2008.

(51) Int. Cl.
*A61N 5/10* (2006.01)
*H01J 35/14* (2006.01)

(52) U.S. Cl. ........ 378/65; 378/138; 315/503; 250/492.3

(58) Field of Classification Search .................... 378/65, 378/138; 250/492.3; 315/503
See application file for complete search history.

(56) References Cited

U.S. PATENT DOCUMENTS 2,306,875 A * 12/1942 Fremlin ....................... 315/5.35
(Continued)

*Primary Examiner* — Edward Glick
*Assistant Examiner* — Thomas R Artman
(74) *Attorney, Agent, or Firm* — Kevin Hazen

(57) ABSTRACT

The invention comprises an X-ray method and apparatus used in conjunction with charged particle or proton beam radiation therapy of cancerous tumors. The system uses an X-ray beam that lies in substantially the same path as a proton beam path of a particle beam cancer therapy system. The system creates an electron beam that strikes an X-ray generation source where the X-ray generation source is located proximate to the proton beam path. By generating the X-rays near the proton beam path, an X-ray path that is essentially the proton beam path is created. Using the generated X-rays, the system collects X-ray images of a localized body tissue region about a cancerous tumor. The generated image is usable for: fine tuning body alignment relative to the proton beam path, to control the proton beam path to accurately and precisely target the tumor, and/or in system verification and validation.

16 Claims, 5 Drawing Sheets

U.S. PATENT DOCUMENTS

| | | | |
|---|---|---|---|
| 3,906,280 A * | 9/1975 | Andelfinger et al. | 313/449 |
| 4,344,011 A * | 8/1982 | Hayashi et al. | 378/138 |
| 4,607,380 A * | 8/1986 | Oliver | 378/138 |
| 4,726,046 A * | 2/1988 | Nunan | 378/65 |
| 4,730,353 A * | 3/1988 | Ono et al. | 378/138 |
| 4,868,844 A | 9/1989 | Nunan | |
| 4,870,287 A | 9/1989 | Cole | |
| 5,017,789 A | 5/1991 | Young | |
| 5,039,867 A | 8/1991 | Nishihara | |
| 5,168,241 A | 12/1992 | Hirota | |
| 5,177,448 A | 1/1993 | Ikeguchi | |
| 5,260,581 A | 11/1993 | Lesyna | |
| 5,285,166 A | 2/1994 | Hiramoto | |
| 5,349,198 A | 9/1994 | Takanaka | |
| 5,363,008 A | 11/1994 | Hiramoto | |
| 5,440,133 A | 8/1995 | Moyers | |
| 5,511,549 A | 4/1996 | Legg | |
| 5,538,494 A | 7/1996 | Matsuda | |
| 5,585,642 A | 12/1996 | Britton | |
| 5,600,213 A | 2/1997 | Hiramoto | |
| 5,626,682 A | 5/1997 | Kobari | |
| 5,633,907 A * | 5/1997 | Gravelle et al. | 378/121 |
| 5,661,366 A | 8/1997 | Hirota | |
| 5,698,954 A | 12/1997 | Hirota | |
| 5,760,395 A | 6/1998 | Johnstone | |
| 5,789,875 A | 8/1998 | Hiramoto | |
| 5,818,058 A | 10/1998 | Nakanishi | |
| 5,820,320 A | 10/1998 | Kobari | |
| 5,825,845 A | 10/1998 | Blair | |
| 5,866,912 A | 2/1999 | Slater | |
| 5,895,926 A | 4/1999 | Britton | |
| 5,907,595 A * | 5/1999 | Sommerer | 378/136 |
| 5,917,293 A | 6/1999 | Saito | |
| 5,969,367 A | 10/1999 | Hiramoto | |
| 5,986,274 A | 11/1999 | Akiyama | |
| 5,993,373 A | 11/1999 | Nonaka | |
| 6,008,499 A | 12/1999 | Hiramoto | |
| 6,034,377 A | 3/2000 | Pu | |
| 6,087,670 A | 7/2000 | Hiramoto | |
| 6,087,672 A | 7/2000 | Matsuda | |
| 6,207,952 B1 | 3/2001 | Kan | |
| 6,218,675 B1 | 4/2001 | Akiyama | |
| 6,236,043 B1 | 5/2001 | Tadokoro | |
| 6,265,837 B1 | 7/2001 | Akiyama | |
| 6,316,776 B1 | 11/2001 | Hiramoto | |
| 6,322,249 B1 | 11/2001 | Wofford | |
| 6,339,635 B1 * | 1/2002 | Schardt et al. | 378/137 |
| 6,365,894 B2 | 4/2002 | Tadokoro | |
| 6,421,416 B1 | 7/2002 | Sliski | |
| 6,433,349 B2 | 8/2002 | Akiyama | |
| 6,433,494 B1 | 8/2002 | Kulish | |
| 6,437,513 B1 | 8/2002 | Stelzer | |
| 6,444,990 B1 | 9/2002 | Morgan | |
| 6,462,490 B1 | 10/2002 | Matsuda | |
| 6,472,834 B2 | 10/2002 | Hiramoto | |
| 6,476,403 B1 | 11/2002 | Dolinskii | |
| 6,560,354 B1 | 5/2003 | Maurer, Jr. | |
| 6,580,084 B1 | 6/2003 | Hiramoto | |
| 6,597,005 B1 | 7/2003 | Badura | |
| 6,600,164 B1 | 7/2003 | Badura | |
| 6,614,038 B1 | 9/2003 | Brand | |
| 6,617,598 B1 | 9/2003 | Matsuda | |
| 6,635,882 B1 | 10/2003 | Pavlovic | |
| 6,639,234 B1 | 10/2003 | Badura | |
| 6,670,618 B1 | 12/2003 | Hartmann | |
| 6,683,318 B1 | 1/2004 | Haberer | |
| 6,710,362 B2 | 3/2004 | Kraft | |
| 6,717,162 B1 | 4/2004 | Jongen | |
| 6,730,921 B2 | 5/2004 | Kraft | |
| 6,736,831 B1 | 5/2004 | Hartmann | |
| 6,745,072 B1 | 6/2004 | Badura | |
| 6,774,383 B2 | 8/2004 | Norimine | |
| 6,777,700 B2 | 8/2004 | Yanagisawa | |
| 6,785,359 B2 * | 8/2004 | Lemaitre | 378/136 |
| 6,787,771 B2 | 9/2004 | Bashkirov | |
| 6,792,078 B2 | 9/2004 | Kato | |
| 6,799,068 B1 | 9/2004 | Hartmann | |
| 6,800,866 B2 | 10/2004 | Amemiya | |
| 6,803,591 B2 | 10/2004 | Muramatsu et al. | |
| 6,809,325 B2 | 10/2004 | Dahl | |
| 6,819,743 B2 | 11/2004 | Kato | |
| 6,822,244 B2 | 11/2004 | Beloussov | |
| 6,823,045 B2 | 11/2004 | Kato | |
| 6,838,676 B1 | 1/2005 | Jackson | |
| 6,859,741 B2 | 2/2005 | Haberer | |
| 6,881,970 B2 | 4/2005 | Akiyama | |
| 6,891,177 B1 | 5/2005 | Kraft | |
| 6,897,451 B2 | 5/2005 | Kaercher | |
| 6,900,446 B2 | 5/2005 | Akiyama | |
| 6,903,351 B1 | 6/2005 | Akiyama | |
| 6,903,356 B2 | 6/2005 | Muramatsu | |
| 6,931,100 B2 | 8/2005 | Kato | |
| 6,936,832 B2 | 8/2005 | Norimine | |
| 6,953,943 B2 | 10/2005 | Yanagisawa | |
| 6,979,832 B2 | 12/2005 | Yanagisawa | |
| 6,984,835 B2 | 1/2006 | Harada | |
| 6,992,312 B2 | 1/2006 | Yanagisawa | |
| 7,012,267 B2 | 3/2006 | Moriyama | |
| 7,026,636 B2 | 4/2006 | Yanagisawa | |
| 7,030,396 B2 | 4/2006 | Muramatsu | |
| 7,045,781 B2 | 5/2006 | Adamec | |
| 7,049,613 B2 | 5/2006 | Yanagisawa | |
| 7,053,389 B2 | 5/2006 | Yanagisawa | |
| 7,054,801 B2 | 5/2006 | Sakamoto | |
| 7,060,997 B2 | 6/2006 | Norimine | |
| 7,071,479 B2 | 7/2006 | Yanagisawa | |
| 7,081,619 B2 | 7/2006 | Bashkirov | |
| 7,084,410 B2 | 8/2006 | Beloussov | |
| 7,091,478 B2 | 8/2006 | Haberer | |
| 7,102,144 B2 | 9/2006 | Matsuda | |
| 7,109,505 B1 | 9/2006 | Sliski | |
| 7,122,811 B2 | 10/2006 | Matsuda | |
| 7,141,810 B2 | 11/2006 | Kakiuchi | |
| 7,154,107 B2 | 12/2006 | Yanagisawa | |
| 7,154,108 B2 | 12/2006 | Tadokoro | |
| 7,173,264 B2 | 2/2007 | Moriyama | |
| 7,173,265 B2 | 2/2007 | Miller | |
| 7,193,227 B2 | 3/2007 | Hiramoto | |
| 7,199,382 B2 | 4/2007 | Rigney | |
| 7,208,748 B2 | 4/2007 | Sliski | |
| 7,212,608 B2 | 5/2007 | Nagamine | |
| 7,212,609 B2 | 5/2007 | Nagamine | |
| 7,227,161 B2 | 6/2007 | Matsuda | |
| 7,247,869 B2 | 7/2007 | Tadokoro | |
| 7,259,529 B2 | 8/2007 | Tanaka | |
| 7,262,424 B2 | 8/2007 | Moriyama | |
| 7,274,018 B2 | 9/2007 | Adamec | |
| 7,274,025 B2 | 9/2007 | Berdermann | |
| 7,280,633 B2 | 10/2007 | Cheng | |
| 7,297,967 B2 | 11/2007 | Yanagisawa | |
| 7,301,162 B2 | 11/2007 | Matsuda | |
| 7,319,231 B2 | 1/2008 | Moriyama | |
| 7,345,292 B2 | 3/2008 | Moriyama | |
| 7,351,988 B2 | 4/2008 | Naumann | |
| 7,355,189 B2 | 4/2008 | Yanagisawa | |
| 7,368,740 B2 | 5/2008 | Beloussov | |
| 7,372,053 B2 | 5/2008 | Yamashita | |
| 7,381,979 B2 | 6/2008 | Yamashita | |
| 7,432,516 B2 | 10/2008 | Peggs | |
| 7,714,309 B2 * | 5/2010 | Mackie et al. | 250/492.3 |
| 7,763,873 B2 * | 7/2010 | Flynn et al. | 250/505.1 |
| 7,801,277 B2 * | 9/2010 | Zou et al. | 378/122 |
| 2008/0191142 A1 | 8/2008 | Pedroni | |
| 2010/0008469 A1 * | 1/2010 | Balakin | 378/65 |
| 2010/0128846 A1 * | 5/2010 | Balakin | 378/62 |

* cited by examiner

CHARGED PARTICLE CANCER THERAPY X-RAY METHOD AND APPARATUS

CROSS REFERENCES TO RELATED APPLICATIONS

This application claims benefit of:
U.S. provisional patent application No. 61/055,395 filed May 22, 2008;
U.S. provisional patent application No. 61/137,574 filed Aug. 1, 2008;
U.S. provisional patent application No. 61/192,245 filed Sep. 17, 2008;
U.S. provisional patent application No. 61/055,409 filed May 22, 2008;
U.S. provisional patent application No. 61/203,308 filed Dec. 22, 2008;
U.S. provisional patent application No. 61/188,407 filed Aug. 11, 2008;
U.S. provisional patent application No. 61/209,529 filed Mar. 9, 2009;
U.S. provisional patent application No. 61/188,406 filed Aug. 11, 2008;
U.S. provisional patent application No. 61/189,815 filed Aug. 25, 2008;
U.S. provisional patent application No. 61/208,182 filed Feb. 23, 2009;
U.S. provisional patent application No. 61/201,731 filed Dec. 15, 2008;
U.S. provisional patent application No. 61/208,971 filed Mar. 3, 2009;
U.S. provisional patent application No. 61/205,362 filed Jan. 21, 2009;
U.S. provisional patent application No. 61/134,717 filed Jul. 14, 2008;
U.S. provisional patent application No. 61/134,707 filed Jul. 14, 2008;
U.S. provisional patent application No. 61/201,732 filed Dec. 15, 2008;
U.S. provisional patent application No. 61/198,509 filed Nov. 7, 2008;
U.S. provisional patent application No. 61/134,718 filed Jul. 14, 2008;
U.S. provisional patent application No. 61/190,613 filed Sep. 2, 2008;
U.S. provisional patent application No. 61/191,043 filed Sep. 8, 2008;
U.S. provisional patent application No. 61/192,237 filed Sep. 17, 2008;
U.S. provisional patent application No. 61/201,728 filed Dec. 15, 2008;
U.S. provisional patent application No. 61/190,546 filed Sep. 2, 2008;
U.S. provisional patent application No. 61/189,017 filed Aug. 15, 2008;
U.S. provisional patent application No. 61/198,248 filed Nov. 5, 2008;
U.S. provisional patent application No. 61/198,508 filed Nov. 7, 2008;
U.S. provisional patent application No. 61/197,971 filed Nov. 3, 2008;
U.S. provisional patent application No. 61/199,405 filed Nov. 17, 2008;
U.S. provisional patent application No. 61/199,403 filed Nov. 17, 2008; and
U.S. provisional patent application No. 61/199,404 filed Nov. 17, 2008,
all of which are incorporated herein in their entirety by this reference thereto.

BACKGROUND OF THE INVENTION

1. Field of the Invention

This invention relates generally to treatment of solid cancers. More particularly, the invention relates to a charged particle cancer therapy X-ray method and apparatus used in conjunction with radiation treatment of cancerous tumors.

2. Discussion of the Prior Art

Cancer

A tumor is an abnormal mass of tissue. Tumors are either benign or malignant. A benign tumor grows locally, but does not spread to other parts of the body. Benign tumors cause problems because of their spread, as they press and displace normal tissues. Benign tumors are dangerous in confined places such as the skull. A malignant tumor is capable of invading other regions of the body. Metastasis is cancer spreading by invading normal tissue and spreading to distant tissues.

Cancer Treatment

Several forms of radiation therapy exist for cancer treatment including: brachytherapy, traditional electromagnetic X-ray therapy, and proton therapy. Each are further described, infra.

Brachytherapy is radiation therapy using radioactive sources implanted inside the body. In this treatment, an oncologist implants radioactive material directly into the tumor or very close to it. Radioactive sources are also placed within body cavities, such as the uterine cervix.

The second form of traditional cancer treatment using electromagnetic radiation includes treatment using X-rays and gamma rays. An X-ray is high-energy, ionizing, electromagnetic radiation that is used at low doses to diagnose disease or at high doses to treat cancer. An X-ray or Röntgen ray is a form of electromagnetic radiation with a wavelength in the range of 10 to 0.01 nanometers (nm), corresponding to frequencies in the range of 30 PHz to 30 EHz. X-rays are longer than gamma rays and shorter than ultraviolet rays. X-rays are primarily used for diagnostic radiography. X-rays are a form of ionizing radiation and as such can be dangerous. Gamma rays are also a form of sub-magnetic radiation and are at frequencies produced by sub-atomic particle interactions, such as electron-positron annihilation or radioactive decay. In the electromagnetic spectrum, gamma rays are generally characterized as electromagnetic radiation having the highest frequency, as having highest energy, and having the shortest wavelength, such as below about 10 picometers. Gamma rays consist of high energy photons with energies above about 100 keV. X-rays are commonly used to treat cancerous tumors. However, X-rays are not optimal for treatment of cancerous tissue as X-rays deposit their highest does of radiation near the surface of the targeted tissue and delivery exponentially less radiation as they penetrate into the tissue. This results in large amounts of radiation being delivered outside of the tumor. Gamma rays have similar limitations.

The third form of cancer treatment uses protons. Proton therapy systems typically include: a beam generator, an accelerator, and a beam transport system to move the resulting accelerated protons to a plurality of treatment rooms where the protons are delivered to a tumor in a patient's body.

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Due to their relatively enormous size, protons scatter less easily in the tissue and there is very little lateral dispersion. Hence, the proton beam stays focused on the tumor shape without much lateral damage to surrounding tissue. All protons of a given energy have a certain range, defined by the Bragg peak, and the dosage delivery to tissue ratio is maximum over just the last few millimeters of the particle's range. The penetration depth depends on the energy of the particles, which is directly related to the speed to which the particles were accelerated by the proton accelerator. The speed of the proton is adjustable to the maximum rating of the accelerator. It is therefore possible to focus the cell damage due to the proton beam at the very depth in the tissues where the tumor is situated. Tissues situated before the Bragg peak receive some reduced dose and tissues situated after the peak receive none.

Synchrotrons

Patents related to the current invention are summarized here.

Proton Beam Therapy System

F. Cole, et. al. of Loma Linda University Medical Center "Multi-Station Proton Beam Therapy System", U.S. Pat. No. 4,870,287 (Sep. 26, 1989) describe a proton beam therapy system for selectively generating and transporting proton beams from a single proton source and accelerator to a selected treatment room of a plurality of patient treatment rooms.

Transport/Scanning Control

K. Matsuda, et. al. "Particle Beam Irradiation Apparatus, Treatment Planning Unit, and Particle Beam Irradiation Method", U.S. Pat. No. 7,227,161 (Jun. 5, 2007); K. Matsuda, et. al. "Particle Beam Irradiation Treatment Planning Unit, and Particle Beam Irradiation Method", U.S. Pat. No. 7,122,811 (Oct. 17, 2006); and K. Matsuda, et. al. "Particle Beam Irradiation Apparatus, Treatment Planning Unit, and Particle Beam Irradiation Method" (Sep. 5, 2006) describe a particle beam irradiation apparatus have a scanning controller that stops output of an ion beam, changes irradiation position via control of scanning electromagnets, and reinitiates treatment based on treatment planning information.

T. Norimine, et. al. "Particle Therapy System Apparatus", U.S. Pat. Nos. 7,060,997 (Jun. 13, 2006); T. Norimine, et. al. "Particle Therapy System Apparatus", 6,936,832 (Aug. 30, 2005); and T. Norimine, et. al. "Particle Therapy System Apparatus", 6,774,383 (Aug. 10, 2004) each describe a particle therapy system having a first steering magnet and a second steering magnet disposed in a charged particle beam path after a synchrotron that are controlled by first and second beam position monitors.

K. Moriyama, et. al. "Particle Beam Therapy System", U.S. Pat. No. 7,012,267 (Mar. 14, 2006) describe a manual input to a ready signal indicating preparations are completed for transport of the ion beam to a patient.

H. Harada, et. al. "Irradiation Apparatus and Irradiation Method", U.S. Pat. No. 6,984,835 (Jan. 10, 2006) describe an irradiation method having a large irradiation filed capable of uniform dose distribution, without strengthening performance of an irradiation field device, using a position controller having overlapping area formed by a plurality of irradiations using a multileaf collimator. The system provides flat and uniform dose distribution over an entire surface of a target.

H. Akiyama, et. al. "Charged Particle Beam Irradiation Equipment Having Scanning Electromagnet Power Supplies", U.S. Pat. No. 6,903,351 (Jun. 7, 2005); H. Akiyama, et. al. "Charged Particle Beam Irradiation Equipment Having Scanning Electromagnet Power Supplies", U.S. Pat. No. 6,900,436 (May 31, 2005); and H. Akiyama, et. al. "Charged Particle Beam Irradiation Equipment Having Scanning Electromagnet Power Supplies", U.S. Pat. No. 6,881,970 (Apr. 19, 2005) all describe a power supply for applying a voltage to a scanning electromagnet for deflecting a charged particle beam and a second power supply without a pulsating component to control the scanning electromagnet more precisely allowing for uniform irradiation of the irradiation object.

K. Amemiya, et. al. "Accelerator System and Medical Accelerator Facility", U.S. Pat. No. 6,800,866 (Oct. 5, 2004) describe an accelerator system having a wide ion beam control current range capable of operating with low power consumption and having a long maintenance interval.

A. Dolinskii, et. al. "Gantry with an Ion-Optical System", U.S. Pat. No. 6,476,403 (Nov. 5, 2002) describe a gantry for an ion-optical system comprising an ion source and three bending magnets for deflecting an ion beam about an axis of rotation. A plurality of quadrupoles are also provided along the beam path to create a fully achromatic beam transport and an ion beam with difference emittances in the horizontal and vertical planes. Further, two scanning magnets are provided between the second and third bending magnets to direct the beam.

H. Akiyama, et. al. "Charged Particle Beam Irradiation Apparatus", U.S. Pat. No. 6,218,675 (Apr. 17, 2001) describe a charged particle beam irradiation apparatus for irradiating a target with a charged particle beam that include a plurality of scanning electromagnets and a quadrupole electromagnet between two of the plurality of scanning electromagnets.

K. Matsuda, et. al. "Charged Particle Beam Irradiation System and Method Thereof", U.S. Pat. No. 6,087,672 (Jul. 11, 2000) describe a charged particle beam irradiation system having a ridge filter with shielding elements to shield a part of the charged particle beam in an area corresponding to a thin region in said target.

P. Young, et. al. "Raster Scan Control System for a Charged-Particle Beam", U.S. Pat. No. 5,017,789 (May 21, 1991) describe a raster scan control system for use with a charged-particle beam delivery system that includes a nozzle through which a charged particle beam passes. The nozzle includes a programmable raster generator and both fast and slow sweep scan electromagnets that cooperate to generate a sweeping magnetic field that steers the beam along a desired raster scan pattern at a target.

Beam Shape Control

M. Yanagisawa, et. al. "Particle Beam Irradiation System and Method of Adjusting Irradiation Field Forming Apparatus", U.S. Pat. No. 7,154,107 (Dec. 26, 2006) and M. Yanagisawa, et. al. "Particle Beam Irradiation System and Method of Adjusting Irradiation Field Forming Apparatus", U.S. Pat. No. 7,049,613 (May 23, 2006) describe a particle therapy system having a scattering compensator and a range modulation wheel. Movement of the scattering compensator and the range modulation wheel adjusts a size of the ion beam and scattering intensity resulting in penumbra control and a more uniform dose distribution to a diseased body part.

T. Haberer, et. al. "Device and Method for Adapting the Size of an Ion Beam Spot in the Domain of Tumor Irradiation", U.S. Pat. No. 6,859,741 (Feb. 22, 2005) describe a method and apparatus for adapting the size of an ion beam in tumor irradiation. Quadrupole magnets determining the size of the ion beam spot are arranged directly in front of raster scanning magnets determining the size of the ion beam spot.

The apparatus contains a control loop for obtaining current correction values to further control the ion beam spot size.

K. Matsuda, et. al. "Charged Particle Irradiation Apparatus and an Operating Method Thereof", U.S. Pat. No. 5,986,274 (Nov. 16, 1999) describe a charged particle irradiation apparatus capable of decreasing a lateral dose falloff at boundaries of an irradiation field of a charged particle beam using controlling magnet fields of quadrupole electromagnets and deflection electromagnets to control the center of the charged particle beam passing through the center of a scatterer irrespective of direction and intensity of a magnetic field generated by scanning electromagnets.

K. Hiramoto, et. al. "Charged Particle Beam Apparatus and Method for Operating the Same", U.S. Pat. No. 5,969,367 (Oct. 19, 1999) describe a charged particle beam apparatus where a the charged particle beam is enlarged by a scatterer resulting in a Gaussian distribution that allows overlapping of irradiation doses applied to varying spot positions.

M. Moyers, et. al. "Charged Particle Beam Scattering System", U.S. Pat. No. 5,440,133 (Aug. 8, 1995) describe a radiation treatment apparatus for producing a particle beam and a scattering foil for changing the diameter of the charged particle beam.

C. Nunan "Multileaf Collimator for Radiotherapy Machines", U.S. Pat. No. 4,868,844 (Sep. 19, 1989) describes a radiation therapy machine having a multileaf collimator formed of a plurality of heavy metal leaf bars movable to form a rectangular irradiation field.

R. Maughan, et. al. "Variable Radiation Collimator", U.S. Pat. No. 4,754,147 (Jun. 28, 1988) describe a variable collimator for shaping a cross-section of a radiation beam that relies on rods, which are positioned around a beam axis. The rods are shaped by a shaping member cut to a shape of an area of a patient go be irradiated.

Beam Energy/Intensity

M. Yanagisawa, et. al. "Charged Particle Therapy System, Range Modulation Wheel Device, and Method of Installing Range Modulation Wheel Device", U.S. Pat. No. 7,355,189 (Apr. 8, 2008) and Yanagisawa, et. al. "Charged Particle Therapy System, Range Modulation Wheel Device, and Method of Installing Range Modulation Wheel Device", U.S. Pat. No. 7,053,389 (May 30, 2008) both describe a particle therapy system having a range modulation wheel. The ion beam passes through the range modulation wheel resulting in a plurality of energy levels corresponding to a plurality of stepped thicknesses of the range modulation wheel.

M. Yanagisawa, et. al. "Particle Beam Irradiation System and Method of Adjusting Irradiation Apparatus", U.S. Pat. No. 7,297,967 (Nov. 20, 2007); M. Yanagisawa, et. al. "Particle Beam Irradiation System and Method of Adjusting Irradiation Apparatus", U.S. Pat. No. 7,071,479 (Jul. 4, 2006); M. Yanagisawa, et. al. "Particle Beam Irradiation System and Method of Adjusting Irradiation Apparatus", U.S. Pat. No. 7,026,636 (Apr. 11, 2006); and M. Yanagisawa, et. al. "Particle Beam Irradiation System and Method of Adjusting Irradiation Apparatus", U.S. Pat. No. 6,777,700 (Aug. 17, 2004) all describe a scattering device, a range adjustment device, and a peak spreading device. The scattering device and range adjustment device are combined together and are moved along a beam axis. The spreading device is independently moved along the axis to adjust the degree of ion beam scattering. Combined, the devise increases the degree of uniformity of radiation dose distribution to a diseased tissue.

A. Sliski, et. al. "Programmable Particle Scatterer for Radiation Therapy Beam Formation", U.S. Pat. No. 7,208,748 (Apr. 24, 2007) describe a programmable pathlength of a fluid disposed into a particle beam to modulate scattering angle and beam range in a predetermined manner. The charged particle beam scatterer/range modulator comprises a fluid reservoir having opposing walls in a particle beam path and a drive to adjust the distance between the walls of the fluid reservoir under control of a programmable controller to create a predetermined spread out Bragg peak at a predetermined depth in a tissue. The beam scattering and modulation is continuously and dynamically adjusted during treatment of a tumor to deposit a dose in a targeted predetermined three dimensional volume.

M. Tadokoro, et. al. "Particle Therapy System", U.S. Pat. No. 7,247,869 (Jul. 24, 2007) and U.S. Pat. No. 7,154,108 (Dec. 26, 2006) each describe a particle therapy system capable of measuring energy of a charged particle beam during irradiation during use. The system includes a beam passage between a pair of collimators, an energy detector mounted, and a signal processing unit.

G. Kraft, et. al. "Ion Beam Scanner System and Operating Method", U.S. Pat. No. 6,891,177 (May 10, 2005) describe an ion beam scanning system having a mechanical alignment system for the target volume to be scanned and allowing for depth modulation of the ion beam by means of a linear motor and transverse displacement of energy absorption means resulting in depth-staggered scanning of volume elements of a target volume.

G. Hartmann, et. al. "Method for Operating an Ion Beam Therapy System by Monitoring the Distribution of the Radiation Dose", U.S. Pat. No. 6,736,831 (May 18, 2004) describe a method for operation of an ion beam therapy system having a grid scanner and irradiates and scans an area surrounding an isocentre. Both the depth dose distribution and the transverse dose distribution of the grid scanner device at various positions in the region of the isocentre are measured and evaluated.

Y. Jongen "Method for Treating a Target Volume with a Particle Beam and Device Implementing Same", U.S. Pat. No. 6,717,162 (Apr. 6, 2004) describes a method of producing from a particle beam a narrow spot directed towards a target volume, characterized in that the spot sweeping speed and particle beam intensity are simultaneously varied.

G. Kraft, et. al. "Device for Irradiating a Tumor Tissue", U.S. Pat. No. 6,710,362 (Mar. 23, 2004) describe a method and apparatus of irradiating a tumor tissue, where the apparatus has an electromagnetically driven ion-braking device in the proton beam path for depth-wise adaptation of the proton beam that adjusts both the ion beam direction and ion beam range.

K. Matsuda, et. al. "Charged Particle Beam Irradiation Apparatus", U.S. Pat. No. 6,617,598 (Sep. 9, 2003) describe a charged particle beam irradiation apparatus that increased the width in a depth direction of a Bragg peak by passing the Bragg peak through an enlarging device containing three ion beam components having different energies produced according to the difference between passed positions of each of the filter elements.

H. Stelzer, et. al. "Ionization Chamber for Ion Beams and Method for Monitoring the Intensity of an Ion Beam", U.S. Pat. No. 6,437,513 (Aug. 20, 2002) describe an ionization chamber for ion beams and a method of monitoring the intensity of an ion therapy beam. The ionization chamber includes a chamber housing, a beam inlet window, a beam outlet window, a beam outlet window, and a chamber volume filled with counting gas.

H. Akiyama, et. al. "Charged-Particle Beam Irradiation Method and System", U.S. Pat. No. 6,433,349 (Aug. 13, 2002) and H. Akiyama, et. al. "Charged-Particle Beam Irradiation Method and System", U.S. Pat. No. 6,265,837 (Jul.

24, 2001) both describe a charged particle beam irradiation system that includes a changer for changing energy of the particle and an intensity controller for controlling an intensity of the charged-particle beam.

Y. Pu "Charged Particle Beam Irradiation Apparatus and Method of Irradiation with Charged Particle Beam", U.S. Pat. No. 6,034,377 (Mar. 7, 2000) describes a charged particle beam irradiation apparatus having an energy degrader comprising: (1) a cylindrical member having a length; and (2) a distribution of wall thickness in a circumferential direction around an axis of rotation, where thickness of the wall determines energy degradation of the irradiation beam.

Dosage

K. Matsuda, et. al. "Particle Beam Irradiation System", U.S. Pat. No. 7,372,053 (Nov. 27, 2007) describe a particle beam irradiation system ensuring a more uniform dose distribution at an irradiation object through use of a stop signal, which stops the output of the ion beam from the irradiation device.

H. Sakamoto, et. al. "Radiation Treatment Plan Making System and Method", U.S. Pat. No. 7,054,801 (May 30, 2006) describe a radiation exposure system that divides an exposure region into a plurality of exposure regions and uses a radiation simulation to plan radiation treatment conditions to obtain flat radiation exposure to the desired region.

G. Hartmann, et. al. "Method For Verifying the Calculated Radiation Dose of an Ion Beam Therapy System", U.S. Pat. No. 6,799,068 (Sep. 28, 2004) describe a method for the verification of the calculated dose of an ion beam therapy system that comprises a phantom and a discrepancy between the calculated radiation dose and the phantom.

H. Brand, et. al. "Method for Monitoring the Irradiation Control of an Ion Beam Therapy System", U.S. Pat. No. 6,614,038 (Sep. 2, 2003) describe a method of checking a calculated irradiation control unit of an ion beam therapy system, where scan data sets, control computer parameters, measuring sensor parameters, and desired current values of scanner magnets are permanently stored.

T. Kan, et. al. "Water Phantom Type Dose Distribution Determining Apparatus", U.S. Pat. No. 6,207,952 (Mar. 27, 2001) describe a water phantom type dose distribution apparatus that includes a closed water tank, filled with water to the brim, having an inserted sensor that is used to determine an actual dose distribution of radiation prior to radiation therapy.

Starting/Stopping Irradiation

K. Hiramoto, et. al. "Charged Particle Beam Apparatus and Method for Operating the Same", U.S. Pat. No. 6,316,776 (Nov. 13, 2001) describe a charged particle beam apparatus where a charged particle beam is positioned, started, stopped, and repositioned repetitively. Residual particles are used in the accelerator without supplying new particles if sufficient charge is available.

K. Matsuda, et. al. "Method and Apparatus for Controlling Circular Accelerator", U.S. Pat. No. 6,462,490 (Oct. 8, 2002) describe a control method and apparatus for a circular accelerator for adjusting timing of emitted charged particles. The clock pulse is suspended after delivery of a charged particle stream and is resumed on the basis of state of an object to be irradiated.

Movable Patient

N. Rigney, et. al. "Patient Alignment System with External Measurement and Object Coordination for Radiation Therapy System", U.S. Pat. No. 7,199,382 (Apr. 3, 2007) describe a patient alignment system for a radiation therapy system that includes multiple external measurement devices that obtain position measurements of movable components of the radiation therapy system. The alignment system uses the external measurements to provide corrective positioning feedback to more precisely register the patient to the radiation beam.

Y. Muramatsu, et. al. "Medical Particle Irradiation Apparatus", U.S. Pat. No. 7,030,396 (Apr. 18, 2006); Y. Muramatsu, et. al. "Medical Particle Irradiation Apparatus", U.S. Pat. No. 6,903,356 (Jun. 7, 2005); and Y. Muramatsu, et. al. "Medical Particle Irradiation Apparatus", U.S. Pat. No. 6,803,591 (Oct. 12, 2004) all describe a medical particle irradiation apparatus having a rotating gantry, an annular frame located within the gantry such that is can rotate relative to the rotating gantry, an anti-correlation mechanism to keep the frame from rotating with the gantry, and a flexible moving floor engaged with the frame is such a manner to move freely with a substantially level bottom while the gantry rotates.

H. Nonaka, et. al. "Rotating Radiation Chamber for Radiation Therapy", U.S. Pat. No. 5,993,373 (Nov. 30, 1999) describe a horizontal movable floor composed of a series of multiple plates that are connected in a free and flexible manner, where the movable floor is moved in synchrony with rotation of a radiation beam irradiation section.

Respiration

K. Matsuda "Radioactive Beam Irradiation Method and Apparatus Taking Movement of the Irradiation Area Into Consideration", U.S. Pat. No. 5,538,494 (Jul. 23, 1996) describes a method and apparatus that enables irradiation even in the case of a diseased part changing position due to physical activity, such as breathing and heart beat. Initially, a position change of a diseased body part and physical activity of the patient are measured concurrently and a relationship therebetween is defined as a function. Radiation therapy is performed in accordance to the function.

Patient Positioning

Y. Nagamine, et. al. "Patient Positioning Device and Patient Positioning Method", U.S. Pat. Nos. 7,212,609 and 7,212,608 (May 1, 2007) describe a patient positioning system that compares a comparison area of a reference X-ray image and a current X-ray image of a current patient location using pattern matching.

D. Miller, et. al. "Modular Patient Support System", U.S. Pat. No. 7,173,265 (Feb. 6, 2007) describe a radiation treatment system having a patient support system that includes a modularly expandable patient pod and at least one immobilization device, such as a moldable foam cradle.

K. Kato, et. al. "Multi-Leaf Collimator and Medical System Including Accelerator", U.S. Pat. No. 6,931,100 (Aug. 16, 2005); K. Kato, et. al. "Multi-Leaf Collimator and Medical System Including Accelerator", U.S. Pat. No. 6,823,045 (Nov. 23, 2004); K. Kato, et. al. "Multi-Leaf Collimator and Medical System Including Accelerator", U.S. Pat. No. 6,819,743 (Nov. 16, 2004); and K. Kato, et. al. "Multi-Leaf Collimator and Medical System Including Accelerator", U.S. Pat. No. 6,792,078 (Sep. 14, 2004) all describe a system of leaf plates used to shorten positioning time of a patient for irradiation therapy. Motor driving force is transmitted to a plurality of leaf plates at the same time through a pinion gear. The system also uses upper and lower air cylinders and upper and lower guides to position a patient.

Imaging

P. Adamee, et. al. "Charged Particle Beam Apparatus and Method for Operating the Same", U.S. Pat. No. 7,274,018 (Sep. 25, 2007) and P. Adamee, et. al. "Charged Particle Beam Apparatus and Method for Operating the Same", U.S. Pat. No. 7,045,781 (May 16, 2006) describe a charged particle beam apparatus configured for serial and/or parallel imaging of an object.

K. Hiramoto, et. al. "Ion Beam Therapy System and its Couch Positioning System", U.S. Pat. No. 7,193,227 (Mar. 20, 2007) describe a ion beam therapy system having an X-ray imaging system moving in conjunction with a rotating gantry.

C. Maurer, et. al. "Apparatus and Method for Registration of Images to Physical Space Using a Weighted Combination of Points and Surfaces", U.S. Pat. No. 6,560,354 (May 6, 2003) described a process of X-ray computed tomography registered to physical measurements taken on the patient's body, where different body parts are given different weights. Weights are used in an iterative registration process to determine a rigid body transformation process, where the transformation function is used to assist surgical or stereotactic procedures.

M. Blair, et. al. "Proton Beam Digital Imaging System", U.S. Pat. No. 5,825,845 (Oct. 20, 1998) describe a proton beam digital imaging system having an X-ray source that is movable into the treatment beam line that can produce an X-ray beam through a region of the body. By comparison of the relative positions of the center of the beam in the patient orientation image and the isocentre in the master prescription image with respect to selected monuments, the amount and direction of movement of the patient to make the best beam center correspond to the target isocentre is determined.

S. Nishihara, et. al. "Therapeutic Apparatus", U.S. Pat. No. 5,039,867 (Aug. 13, 1991) describe a method and apparatus for positioning a therapeutic beam in which a first distance is determined on the basis of a first image, a second distance is determined on the basis of a second image, and the patient is moved to a therapy beam irradiation position on the basis of the first and second distances.

Problem

There exists in the art of particle beam therapy of cancerous tumors a need for positioning and verification of proper positioning of a patient immediately prior to and/or concurrently with particle beam therapy irradiation to ensure targeted and controlled delivery of energy to the cancerous tumor with minimization of damage to surrounding healthy tissue.

SUMMARY OF THE INVENTION

The invention comprises a charged particle cancer therapy X-ray method and apparatus.

DETAILED DESCRIPTION OF THE INVENTION

The invention comprises a charged particle cancer therapy X-ray method and apparatus.

Accurate and precise delivery of protons to a tumor in body tissue is critical in charged particle beam therapy. Complicating accurate and precise deliver is natural movement of the body. Movement of the body occurs on multiple levels, including: (1) general movement; (2) standing, sitting, or lying position variation; and (3) relative movement of internal body parts, such as organs. All of these movements change with time. Hence, a method of determining position of elements of the body at or in close proximity in time to the charged particle therapy is needed, such as after the body is positioned relative to a charged particle beam. Herein, an X-ray positioning and/or verification method and apparatus used in conjunction with charged particle therapy is described.

The system uses an X-ray beam that lies in substantially the same path as a charged particle beam path of a particle beam cancer therapy system. The system creates an electron beam that strikes an X-ray generation source where the X-ray generation source is located proximate to the charged particle beam path. By generating the X-rays near the charged particle beam path, an X-ray path running collinear, in parallel with, and/or substantially in contact with the charged particle beam path is created. The system then collects X-ray images of localized body tissue region about a cancerous tumor. Since, the X-ray path is essentially the charged particle beam path, the generated image is usable for fine tuning body alignment relative to the charged particle beam path, is used to control the charged particle beam path to accurately and precisely target the tumor, and/or is used in system verification and validation.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system. Any charged particle beam system is equally applicable to the techniques described herein.

Figure 1:
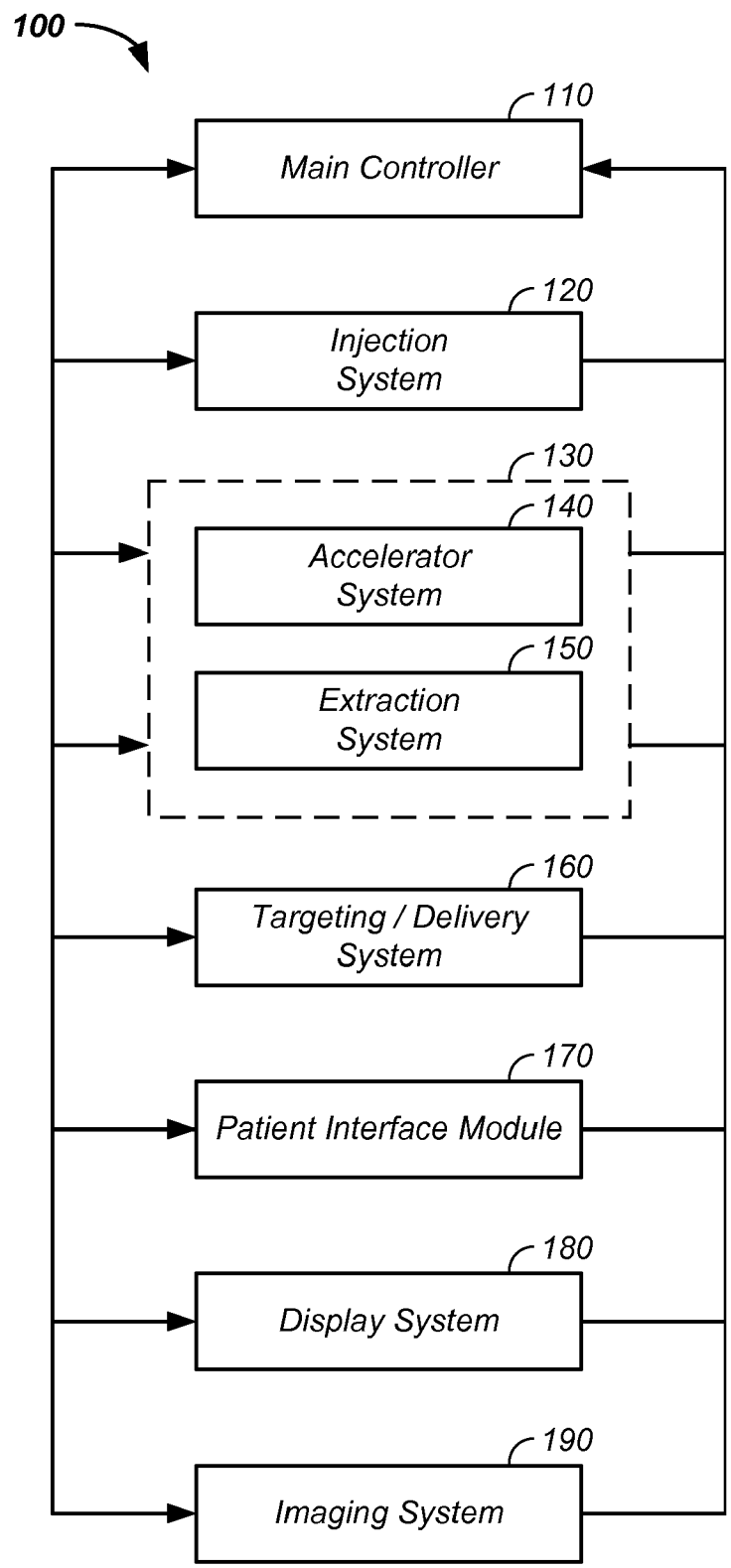
FIG. 1 illustrates sub-system connections of a particle beam therapy system.

Referring now to FIG. 1, a charged particle beam system 100 is illustrated. A charged particle beam, preferably comprises a number of subsystems including any of: a main controller 110; an injection system 120; a synchrotron 130 that typically includes: (1) an accelerator system 140 and (2) an extraction system 150; a targeting/delivery system 160; a patient interface module 170; a display system 180, and/or an imaging system 190.

An exemplary method of use of the charged particle beam system 100 is provided. The main controller 110 controls one or more of the subsystems to accurately and precisely deliver protons to a patient. For example, the main controller 110 obtains an image, such as a portion of a body and/or of a tumor, from the imaging system 190. The main controller 110 also obtains position and/or timing information from the patient interface module 170. The main controller 110 then optionally controls the injection system 120 to inject a proton into a synchrotron 130. The synchrotron typically contains at least an accelerator system 140 and extraction system 150. The main controller preferably controls the proton beam within the accelerator system, such as by controlling speed, trajectory, and timing of the proton beam. The main controller then controls extraction of a proton beam from the accelerator through the extraction system 150. For example, the controller controls timing, energy, and intensity of the extracted beam. The controller 110 also preferably controls targeting of the proton beam through the targeting/delivery system 160 to the patient interface module 170. One or more components of the patient interface module 170 are preferably controlled by the main controller 110. Further, display elements of the display system 180 are preferably controlled via the main controller 110. Displays are typically provided to one or more operators and/or to one or more patients. In one embodiment, the main controller 110 times the delivery of the proton beam from all systems, such that protons are delivered in an optimal therapeutic manner to the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

Synchrotron

Herein, the term synchrotron is used to refer to a system maintaining the charged particle beam in a circulating path; however, cyclotrons are alternatively used, albeit with their inherent limitations of energy, intensity, and extraction control. Further, the charged particle beam is referred to herein as circulating along a circulating path about a central point of the synchrotron. The circulating path is alternatively referred to as an orbiting path; however, the orbiting path does not refer a perfect circle or ellipse, rather it refers to cycling of the protons around a central region.

Figure 2:
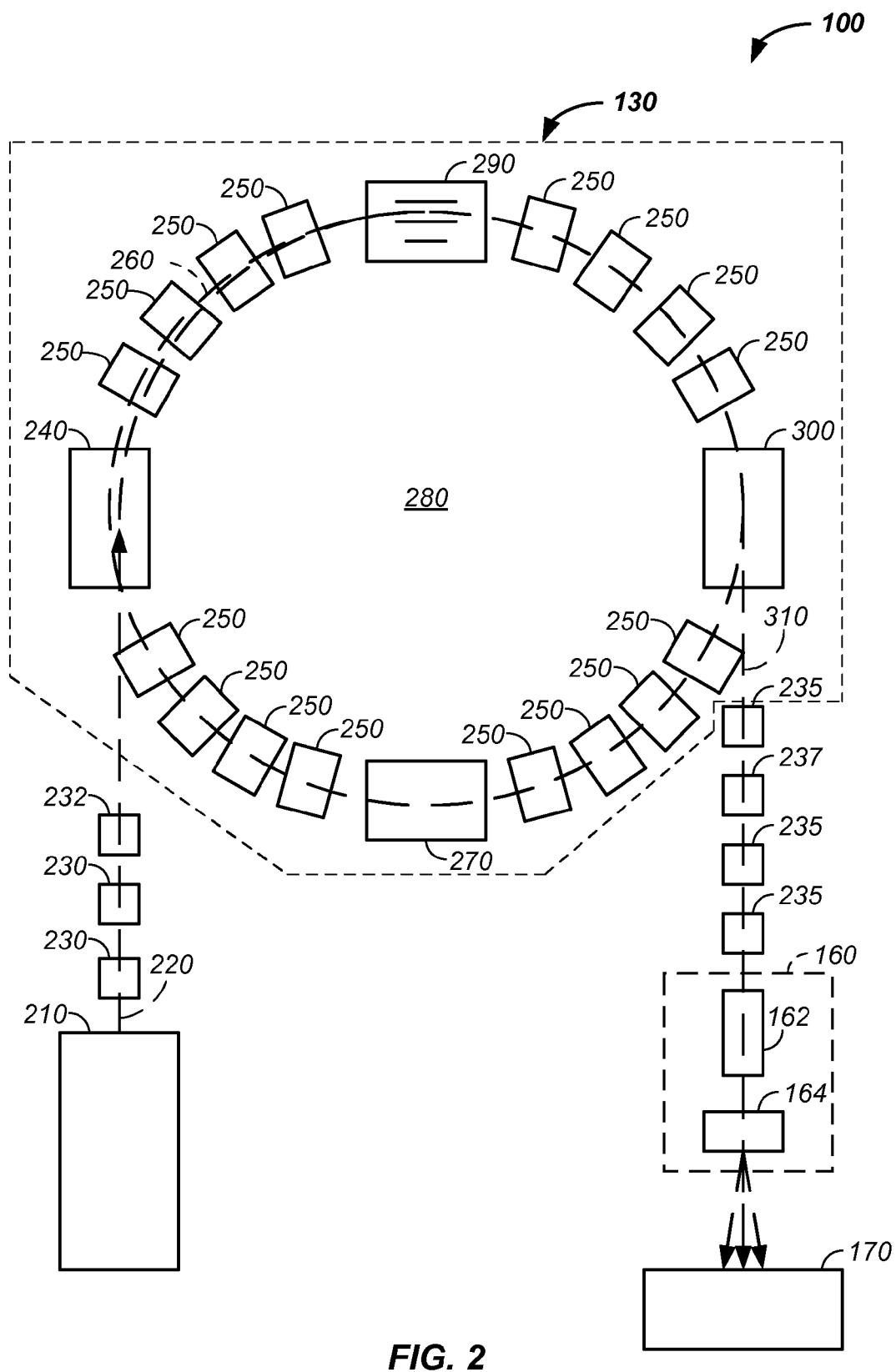
FIG. 2 illustrates a synchrotron.

Referring now to FIG. 2, an illustrative exemplary embodiment of one version of the charged particle beam system 100 is provided. In the illustrated embodiment, a charged particle beam source 210 generates protons. The protons are delivered into a vacuum tube that runs into, through, and out of the synchrotron. The generated protons are delivered along an initial path 220. Focusing magnets 230, such as quadrupole magnets or injection quadrupole magnets, are used to focus the proton beam path. A quadrupole magnet is a focusing magnet. An injector bending magnet 232 bends the proton beam toward the plane of the synchrotron 130. The focused protons having an initial energy are introduced into an injector magnet 240, which is preferably an injection Lamberson magnet. Typically, the initial beam path 262 is along an axis off of, such as above, a circulating plane of the synchrotron 130. The injector bending magnet 232 and injector magnet 240 combine to move the protons into the synchrotron 130. Circulating magnets or main bending magnets 250 are used to turn the protons along a circulating beam path 260. The circulating magnets 250 bend the original beam path 220 into a circulating beam path 260. In this example, the circulating magnets 250 are represented as four sets of four magnets to maintain the circulating beam path 260 into a stable circulating beam path. A plurality of main bending magnets make up a turning section of the synchrotron. In the illustrated exemplary embodiment, four main bending magnets make up a turning section turning the proton beam about ninety degrees. Optionally, any number of magnets or sets of magnets are optionally used to move the protons around a single orbit in the circulation process. The protons pass through an accelerator 270. The accelerator accelerates the protons in the beam path 260. As the protons are accelerated, the fields applied by the magnets are increased. Particularly, the speed of the protons achieved by the accelerator 270 are synchronized with magnetic fields of the circulating magnets 250 to maintain stable circulation of the protons about a central point or region 280 of the synchrotron. At separate points in time the accelerator 270/circulating magnet 250 combination is used to accelerate and/or decelerate the circulating protons. An extraction system 290 is used in combination with a deflector 300 to remove protons from their circulating path 260 within the synchrotron 190. One example of a deflector component is a Lamberson magnet. Typically the deflector moves the protons from the circulating plane to an axis off of the circulating plane, such as above the circulating plane. Extracted protons are preferably directed and/or focused using an extraction bending magnet 237 and extraction focusing magnets 235, such as quadrupole magnets along a transport path into the scanning/targeting/delivery system 160. Two components of a targeting system 160 typically include a first axis control 162, such as a vertical control, and a second axis control 164, such as a horizontal control. Protons are delivered with control to the patient interface module 170 and to a tumor of a patient. Preferably no quadrupoles are used in or around the circulating path of the synchrotron.

Imaging System

Herein, an X-ray system is used to illustrate an imaging system.

Timing

An X-ray is preferably collected either (1) just before or (2) concurrently with treating a subject with proton therapy for a couple of reasons.

First, movement of the body, described supra, changes the local position of the tumor in the body. If the subject has an X-ray taken and is then bodily moved to a proton treatment room, accurate alignment of the proton beam to the tumor is problematic. Alignment of the proton beam to the tumor using one or more X-rays is best performed at the time of proton delivery or in the seconds or minutes immediately prior to proton delivery and after the patient is placed into a therapeutic body position, which is typically a fixed position.

Second, the X-ray taken after positioning the patient is used for verification of proton beam alignment to a targeted position, such as a tumor and/or internal organ position.

Positioning

An X-ray is preferably taken just before treating the subject to aid in patient positioning. For positioning purposes, an X-ray of a large body area is not needed. In one embodiment, an X-ray of only a local area is collected. When collecting an X-ray, the X-ray has an X-ray path. The proton beam has a proton beam path. Overlaying the X-ray path with the proton beam path is one method of aligning the proton beam to the tumor. However, this method involves putting the X-ray equipment into the proton beam path, taking the X-ray, and then moving the X-ray equipment out of the beam path. This process takes time. The elapsed time while the X-ray equipment moves has a couple of detrimental effects. First, during the time required to move the X-ray equipment, the body moves. The resulting movement decreases precision and accuracy of subsequent proton beam alignment to the tumor. Second, the time require to move the X-ray equipment is time that the proton beam therapy system is not in use, which decreases the total efficiency of the proton beam therapy system.

Figure 3:
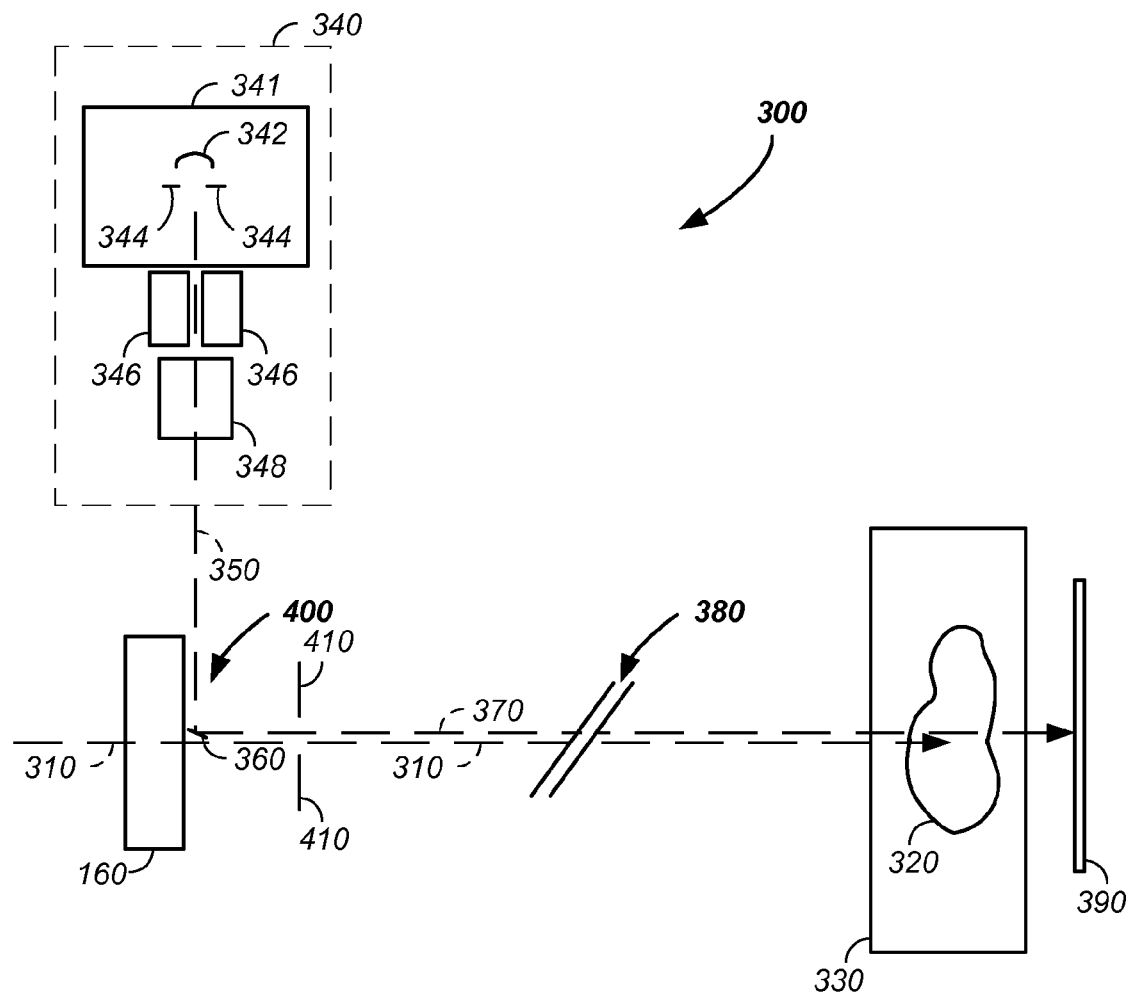
FIG. 3 illustrates an X-ray source proximate a particle beam path.

Referring now to FIG. 3, in one embodiment, an X-ray is generated close to, but not in, the proton beam path. A proton beam therapy system and an X-ray system combination 300 is illustrated in FIG. 3. The proton beam therapy system has a proton beam 310 in a transport system after the deflector 300 of the synchrotron 190. The proton beam is directed by the targeting/delivery system 160 to a tumor 320 of a patient 330. The X-ray system includes an electron beam source 340 generating an electron beam 350. The electron beam is directed to an X-ray generation source 360, such as a piece of tungsten. Preferably, the tungsten X-ray source is located about 1, 2, 3, 5, 10, or 20 millimeters from the proton beam path 310. When the electron beam 35 hits the tungsten, X-rays are generated in all directions. X-rays are optionally blocked with a port 410 and are selected for an X-ray beam path 370. The X-ray beam path 370 and proton beam path 310 run substantially in parallel to the tumor 320. The distance between the X-ray beam path 370 and proton beam path diminishes to near zero and/or the X-ray beam path 370 and proton beam path 310 overlap by the time they reach the tumor 320. Simple geometry shows this to be the case given the long distance, of at least a meter, between the tungsten and the tumor 320. The distance is illustrated as a gap 380 in FIG. 3. The X-rays are detected at an X-ray detector 390, which is used to form an image of the tumor 320 and/or position of the patient 330.

X-Ray Source Lifetime

Preferably, components in the particle beam therapy system require minimal or no maintenance over the lifetime of the particle beam therapy system. For example, it is desirable to equip the proton beam therapy system with an X-ray system having a long lifetime source, such as a lifetime of about 20 years.

In one system, described infra, electrons are used to create X-rays. The electrons are generated at a cathode where the lifetime of the cathode is temperature dependent. Analogous to a light bulb, where the filament is kept in equilibrium, the cathode temperature is held in equilibrium at temperatures at about 200, 500, or 1000 degrees Celsius. Reduction of the cathode temperature results in increased lifetime of the cathode. Hence, the cathode used in generating the electrons is preferably held at as low of a temperature as possible. However, if the temperature of the cathode is reduced, then electron emissions also decrease. To overcome the need for more electrons at lower temperatures, a large cathode is used and the generated electrons are concentrated. The process is analogous to compressing electrons in an electron gun; however, here the compression techniques are adapted to apply to enhancing an X-ray tube lifetime.

Referring still to FIG. 3, an example of an X-ray generation device having an enhanced lifetime is provided. Electrons 350 are generated at a cathode 342, focused with a control electrode 344, and accelerated and/or focused with a series of accelerating electrodes 346 and/or magnetic lenses 348. The accelerated electrons impact an X-ray generation source 360 resulting in generated X-rays that are then directed along an X-ray path 370 to the subject 330. The concentrating of the electrons from a first diameter to a second diameter allows the cathode to operate at a reduced temperature and still yield the necessary amplified level of electrons at the X-ray generation source 360. In one example, the X-ray generation source is the anode coupled with the cathode and/or the X-ray generation source is substantially composed of tungsten.

A more detailed description of an exemplary X-ray generation device is described. An anode/cathode pair is used to generated electrons. The electrons are generated at the cathode having a first diameter, which is denoted $d_1$. The control electrodes attract the generated electrons. For example, if the cathode is held at about −150 kV and the control electrode is held at about −149 kV, then the generated electrons are attracted toward the control electrodes and focused. A series of accelerating electrodes are then used to accelerate the electrons into a substantially parallel path with a smaller diameter, which is denoted $d_2$. For example, with the cathode held at −150 kV, a first, second, third, and fourth accelerating electrodes are held at about −120, −90, −60, and −30 kV, respectively. If a thinner body part is to be analyzed, then the cathode is held at a smaller level, such as about −90 kV and the control electrode, first, second, third, and fourth electrode are each adjusted to lower levels. Generally, the voltage difference from the cathode to fourth electrode is less for a smaller negative voltage at the cathode and vise-versa. The accelerated electrons are optionally passed through a magnetic lens for adjustment of beam size, such as a cylindrical magnetic lens. The electrons are also optionally focused using quadrupole magnets, which focus in one direction and defocus in another direction. The accelerated electrons, which are now adjusted in beam size and focused strike an X-ray generation source, such as tungsten, resulting in generated X-rays that pass through a blocker and proceed along an X-ray path to the subject. The X-ray generation source is optionally cooled with a cooling element, such as water touching or thermally connected to a backside of the X-ray generation source. The concentrating of the electrons from a first diameter to a second diameter allows the cathode to operate at a reduced temperature and still yield the necessary amplified level of electrons at the X-ray generation source.

More generally, the X-ray generation device produces electrons having initial vectors. One or more of the control electrode, accelerating electrodes, magnetic lens, and quadrupole magnets combine to alter the initial electron vectors into parallel vectors with a decreased cross-sectional area having a substantially parallel path, referred to as the accelerated electrons. The process allows the X-ray generation device to operate at a lower temperature. Particularly, instead of using a cathode that is the size of the electron beam needed, a larger electrode is used and the resulting electrons are focused and/or concentrated into the required electron beam needed. As lifetime is roughly an inverse of current density, the concentration of the current density results in a larger lifetime of the X-ray generation device. A specific example is provided for clarity. If the cathode has a fifteen mm radius or $d_1$ is about 30 mm, then the area ($\pi r^2$) is about 225 mm² times pi. If the concentration of the electrons achieves a radius of five mm or $d_2$ is about 10 mm, then the area ($\pi r^2$) is about 25 mm² times pi. The ratio of the two areas is about nine (225π/25π). Thus, there is about nine times less density of current at the larger cathode compared to the traditional cathode having an area of the desired electron beam. Hence, the lifetime of the larger cathode approximates nine times the lifetime of the traditional cathode, though the actual current through the larger cathode and traditional cathode is about the same. Preferably, the area of the cathode is about 2, 4, 6, 8, 10, 15, 20, or 25 times that of the cross-sectional area of the substantially parallel electron beam 2150.

Electron Beam/X-Ray Geometry

Figure 4:
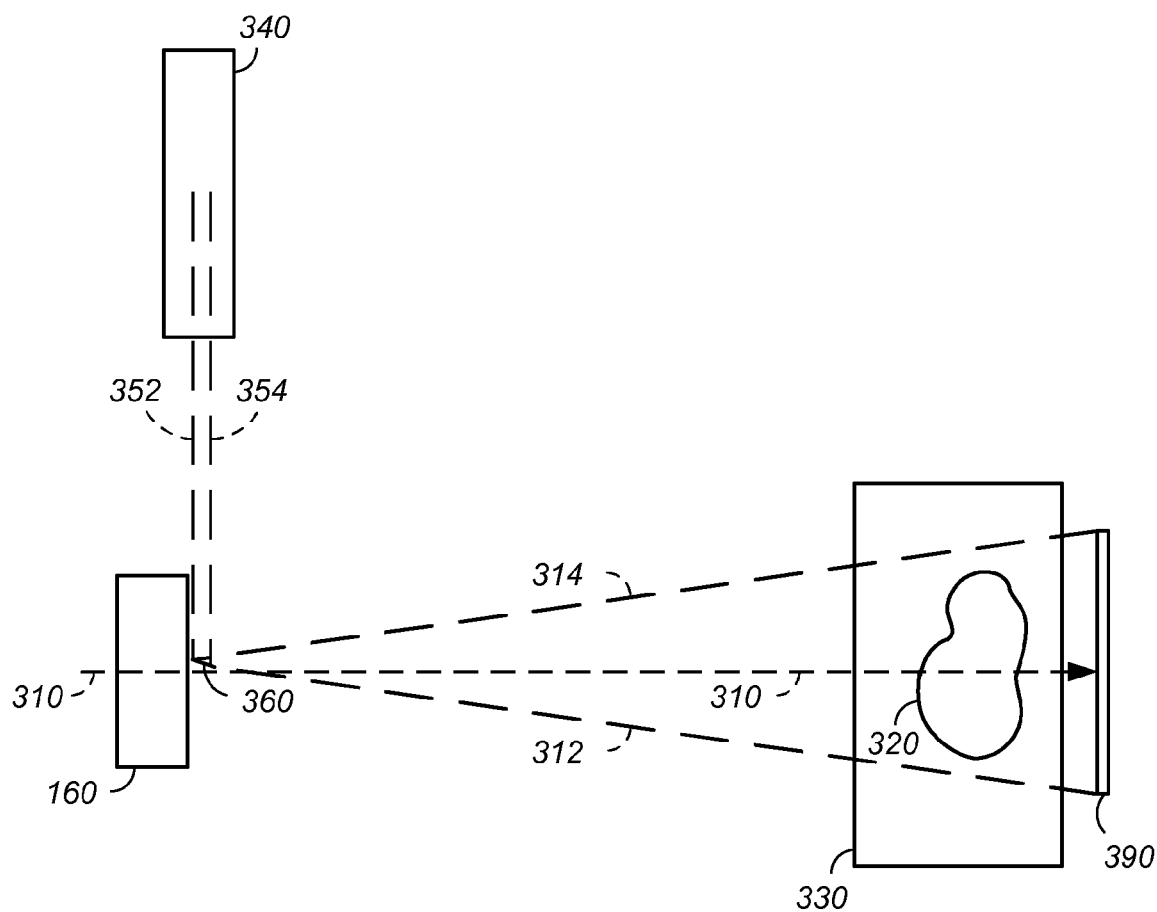
FIG. 4 illustrates an expanded X-ray beam path.

Referring now to FIG. 4, an additional optional geometry configuration of the electron beam path 350 and X-ray beam path 370 shown in FIG. 3 is presented. Particularly, the electron beam 350 is shown as an expanded beam path 352, 354. Also, the X-ray beam path 370 is shown as an expanded beam path 312, 314. Still further, the proton beam path 310 is illustratively shown as scanning from the bottom of the tumor along a lower proton beam path 312 to the top of the tumor along an upper proton beam path 314. The region 400 where the electron beam 350 hits the X-ray generation source 360 to yield X-rays and an X-ray beam 370 is expanded in FIG. 5.

Figure 5:
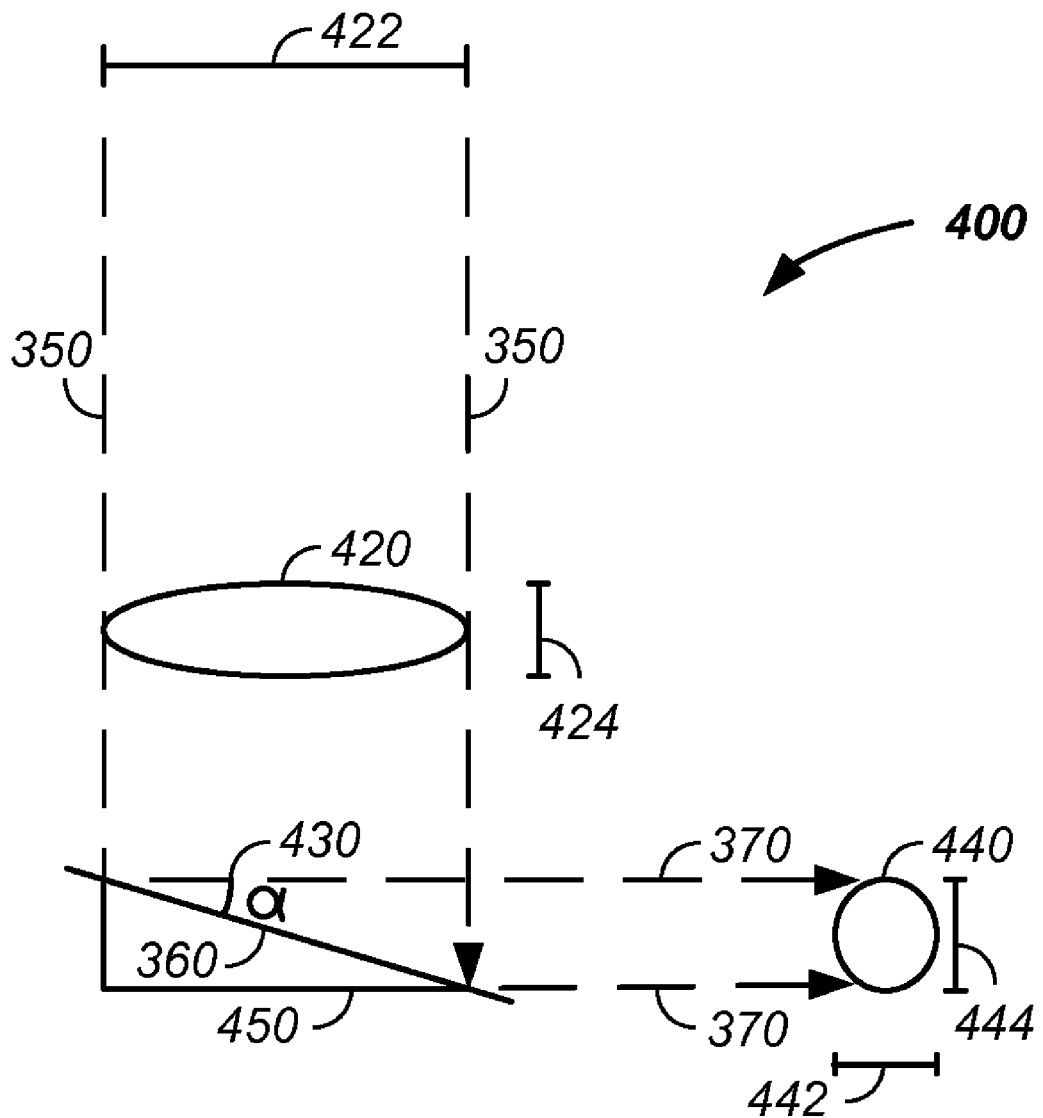
FIG. 5 illustrates geometry of an electron and X-ray beam path.

In another embodiment of the invention, the quadrupole magnets result in an oblong cross-sectional shape of the electron beam. A projection of the oblong cross-sectional shape of the electron beam onto the X-ray generation source results in an X-ray beam that has a small spot in cross-sectional view, which is preferably substantially circular in cross-sectional shape, that is then passed through the patient. The small spot is used to yield an X-ray having enhanced resolution at the patient. Referring now to FIG. 5, additional geometry of the electron beam path 350 and X-ray beam path 370 is illustrated. The electron beam cross section 420 is generally of an oblong or elliptical shape. For example, the electron beam cross section 420 has a height 424 of about three millimeters and a width 422 of about ten millimeters. The oblong shape of electrons hits the X-ray generation source 360, which is set at an angle alpha 430 off of the proton beam path 310. An exemplary angle alpha is about fifteen degrees or less preferably five to forty-five degrees. Generated X-rays are blocked with a port 410. As a result of the geometry of the electron beam path 350, X-ray generation source 360, angle alpha 430, and port 410, the resulting X-ray beam path 370 has a cross-sectional profile 440 that is generally spot shaped having a height 444 and a width 442. For example, the height 444 is about three millimeters and the width of the spot 440 is about three millimeters.

Still referring to FIG. 5, more generally the electron beam path 350, X-ray generation source, angle alpha, and port are optionally configured to result in the spot 440 being an ellipse or rectangular cross section of any dimension. For example, the electron beam path is optionally controlled to have a width of about 1 to 10 millimeter and a height of about 1 to 20 millimeters to result in a spot 440 having a diameter of about 0.5, 1, 2, 4, or 10 millimeters or to have a rectangular shape with sides of about 1, 2, 5, or 10 millimeters. Further, the system allows the X-ray beam path to expand in cross sectional dimension as the path approaches the tumor 320 to allow for imaging of the tumor.

The X-ray generation source, or tungsten material, is preferably cooled with a cooling element 450. The cooling element is preferably a chamber containing a coolant, such as water, a water or alcohol based solution, or a solution containing ethylene glycol. The cooling system is preferably in direct thermal contact with a back side of the tungsten, where the front side of the tungsten is impacted by the electron beam 350 in generation of the X-ray beam 370. The coolant is contained in a container. The coolant is passive, internally circulated, or circulated through an external heat exchange unit. The cooling system alternatively uses heat sinks to remove heat from the tungsten with or without the liquid cooling system.

As a whole, the system generates an X-ray beam that lies in substantially the same path as the proton therapy beam. The X-ray beam is generated by striking a tungsten or equivalent material with an electron beam. The X-ray generation source is located proximate to the proton beam path. Geometry of the incident electrons, geometry of the X-ray generation material, and geometry of the optional X-ray beam blocker 410 yield an X-ray beam that runs either in substantially in parallel with the proton beam or results in an X-ray beam path that starts proximate the proton beam path an expands to cover and transmit through a tumor cross-sectional area to strike an X-ray detector array or film allowing imaging of the tumor from a direction and alignment of the proton therapy beam. The X-ray image is then used to control the charged particle beam path to accurately and precisely target the tumor, and/or is used in system verification and validation.

Having an X-ray generation source that is proximate the proton beam path allows for an X-ray of the patient to be collected close in time to use of the proton beam for tumor therapy as the X-ray generation source need not be mechanically moved prior to proton therapy. For instance, proton irradiation of the tumor occurs within about 1, 5, 10, 20, 30, or 60 seconds of when the X-ray is collected. Although the invention has been described herein with reference to certain preferred embodiments, one skilled in the art will readily appreciate that other applications may be substituted for those set forth herein without departing from the spirit and scope of the present invention.

The invention claimed is:

1. An X-ray apparatus as part of a particle beam cancer therapy system, said particle beam cancer therapy system irradiating a tumor of a patient with a charged particle beam during use, said apparatus comprising:
an X-ray generation source located within forty millimeters of the charged particle beam, wherein said X-ray source maintains a single static position: (1) during use of said X-ray source and (2) during tumor treatment with the charged particle beam; and
a synchrotron accelerating the charged particle beam, wherein said synchrotron comprises exactly four, ninety degree, turning sections,
wherein the tumor is targeted using X-ray images collected using X-rays from said X-ray generation source,
wherein the tumor is treated using the charged particle beam, and
wherein X-rays emitted from said X-ray source run substantially in parallel with the charged particle beam.

2. The apparatus of claim 1, wherein said X-ray generation source comprises a tungsten anode.

3. The apparatus of claim 2, further comprising:
an electron generating cathode;
a control electrode;
a plurality of accelerating electrodes;
a magnetic lens; and
a quadrupole magnet, all of said control electrode, said accelerating electrodes, said magnetic lens, and said quadrupole magnet located between said cathode and an X-ray generating anode in said X-ray generation source, said control electrode, said accelerating electrodes, said magnetic lens, and said quadrupole magnet combining to form a substantially parallel electron beam with an electron beam cross-sectional area, wherein a cross-sectional area of said cathode is greater than about eight times that of the electron beam cross-sectional area.

4. The apparatus of claim 3, wherein said substantially parallel electron beam comprises an oblong cross-sectional shape, wherein geometry of said X-ray generation source yields an X-ray beam comprising a nearly circular cross sectional shape when struck by the electron beam having said oblong cross-sectional shape, the X-ray beam running substantially in parallel with the charged particle beam.

5. The apparatus of claim 4, further comprising a cooling element connected to a backside of said tungsten anode.

6. The apparatus of claim 1, wherein use of said X-ray generation source occurs within thirty seconds of subsequent use of the charged particle beam for tumor therapy.

7. The apparatus of claim 1, wherein said synchrotron comprises:
exactly four turning sections; and
no quadrupoles in the circulating path of the synchrotron.

8. An X-ray method as part of a particle beam cancer therapy system, said particle beam cancer therapy system irradiating a tumor of a patient with a charged particle beam during use, said method comprising the steps of:
generating X-rays with an X-ray generation source located within forty millimeters of the charged particle beam, wherein said X-ray source maintains a single static position: (1) during use of said X-ray source and (2) during tumor treatment with the charged particle beam;
accelerating the charged particle beam with a synchrotron, wherein said synchrotron comprises:
exactly four turning sections; and
no quadrupoles in the circulating path of the synchrotron;
targeting the tumor targeted using X-ray images collected using X-rays from said X-ray generation source; and
treating the tumor using the charged particle beam,
wherein the X-rays emitted from said X-ray source run substantially in parallel with the charged particle beam.

9. The method of claim 8, wherein said X-ray generation source comprises a tungsten anode.

10. The method of claim 9, further comprising the step of:
generating electrons with a cathode, said cathode having a first cross-sectional distance, wherein the X-rays are generated by the electrons from said cathode striking said tungsten anode.

11. The method of claim 10, further comprising the steps of:
focusing the electrons from said first cross-sectional distance to a second cross-sectional distance with a focusing control electrode; and
accelerating the electrons with accelerating electrodes, said focusing control electrode and said accelerating electrodes located between said cathode and said anode.

12. The method of claim 10, further comprising the step of:
forming a substantially parallel electron beam with a control electrode, accelerating electrodes, a magnetic lens, and a quadrupole magnet, all of said control electrode, said accelerating electrodes, said magnetic lens, and said quadrupole magnet located between said cathode and said anode,
wherein the electron beam comprises a cross-sectional area, wherein a cross-sectional area of said cathode is greater than about eight times that of the electron beam cross-sectional area.

13. The method of claim 12, further comprising the step of:
forming a substantially circular cross-section X-ray beam, wherein said substantially parallel electron beam comprises an oblong cross-sectional shape, wherein geometry of said X-ray generation source yields the substantially circular cross section X-ray when struck by the electron beam having said oblong cross-sectional shape, the X-ray beam running substantially in parallel with the charged particle beam.

14. The method of claim 12, further comprising the step of:
cooling said tungsten anode with a cooling element connected to a backside of said tungsten anode.

15. The method of claim 8, further comprising the step of:
using said X-ray generation source within thirty seconds of subsequent use of the charged particle beam for tumor therapy.

16. The method of claim 8, wherein said synchrotron comprises:
exactly four, ninety degree, turning sections.

\* \* \* \* \*